(12) United States Patent
Benderly et al.

(10) Patent No.: US 7,906,699 B2
(45) Date of Patent: Mar. 15, 2011

(54) PROCESSES FOR PRODUCING ETHYLENE AND CARBON MONOXIDE MIXTURES FROM ETHANE

(75) Inventors: Abraham Benderly, Elkins Park, PA (US); Scott Han, Lawrenceville, NJ (US); Mark Anthony Silvano, New Hope, PA (US); Donald Lee Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 316 days.

(21) Appl. No.: 12/221,591

(22) Filed: Aug. 5, 2008

(65) Prior Publication Data

US 2009/0048411 A1 Feb. 19, 2009

Related U.S. Application Data

(60) Provisional application No. 60/964,733, filed on Aug. 14, 2007.

(51) Int. Cl.
*C07C 5/02* (2006.01)
(52) U.S. Cl. ......... 585/654; 585/661; 585/656; 585/659
(58) Field of Classification Search .................. None
See application file for complete search history.

(56) References Cited

U.S. PATENT DOCUMENTS

| | | | |
|---|---|---|---|
| 2,604,495 A | 7/1952 | Erkko | |
| 3,530,109 A | 9/1970 | Fenton | |
| 3,694,412 A | 9/1972 | Nozaki | |
| 4,408,079 A | 10/1983 | Merger et al. | |
| 5,218,146 A * | 6/1993 | Takata et al. | 562/535 |
| 6,284,919 B1 | 9/2001 | Pearson et al. | |
| 6,982,343 B2 | 1/2006 | Chaturvedi et al. | |
| 7,049,466 B2 | 5/2006 | Bogan, Jr. et al. | |
| 7,767,770 B2 * | 8/2010 | Han et al. | 526/75 |
| 2006/0122055 A1 * | 6/2006 | Gaffney et al. | 502/208 |

FOREIGN PATENT DOCUMENTS

| | | |
|---|---|---|
| CN | 1152566 | 6/1997 |
| CN | 1199652 | 11/1998 |
| CN | 1258667 | 7/2000 |
| CN | 1339336 | 3/2002 |
| CN | 1401430 | 3/2003 |
| CN | 1718277 | 1/2006 |
| EP | 0261264 | 3/1988 |

OTHER PUBLICATIONS

Bhasin, et al., "Dehydrogenation and Oxydehydrogenation of Paraffins to Olefins", Applied Catalysis, vol. 221, No. 1-2, pp. 397-419 (2001).
Krylov, et al., "Catalytic Oxidation of Hydrocarbons and Alcohols by Carbon Dioxide on Oxide Catalysts", Ind. Eng. Chem. Res., vol. 34, pp. 474-482 (1995).
Krylov, et al., "The Regularities in the Interaction of Alkanes with CO2 on Oxide Catalysts", Catalysis Today, vol. 24, pp. 371-375 (1995).
Wang, et al., "Dehydrogenation of Ethane with Carbon Dioxide Over Supported Chromium Oxide Catalysts", Applied Catalysis, vol. 196, No. 1, pp. 1-8 (2000).
Li, et al, "Estimation of Consecutive and Parallel Reactions During Ethane Dehydrogenation with Carbon Dioxide Over Co-MCM-41", Polish J. Chem., vol. 79, pp. 1357-1364 (2005).
Naoki, et al., "High-Performance Cr/H-ZSM-5 Catalysts for Oxidative Dehydrogenation of Ethane to Ethylene with CO2 as an Oxidant", Catalysis Comm., vol. 3, pp. 257-262 (2002).
Shaobin, et al., "Effect of Promoters on Catalytic Performance of Cr/SiO2 Catalysts in Oxidative Dehydrogenation . . . ", Catalysis Letters, vol. 73, No. 2-4, pp. 107-111 (2001).
Schmidt, et al., "New Ways to Make Old Chemicals", AIChE Journal, vol. 46, No. 8, pp. 1492-1495 (2000).
Dury, et al., "The active role of CO2 at low temperature in oxidation processes: the case of the oxidative dehydrogenation . . . ", Applied Catalysis, vol. 242, pp. 187-203, (2003).

\* cited by examiner

*Primary Examiner* — Tam M Nguyen
(74) *Attorney, Agent, or Firm* — Kenneth Crimaldi

(57) ABSTRACT

A method for producing a mixture of ethylene and carbon monoxide by contacting ethane and an oxygen source at a temperature of at least 500° C. to produce ethylene and carbon monoxide. A method for producing an alkyl propionate by steps of: (a) contacting ethane and an oxygen source at a temperature of at least 500° C. to produce ethylene; (b) contacting an alcohol, ethylene and carbon monoxide with an ethylene carbonylation catalyst to produce the alkyl propionate; and (c) separating the alkyl propionate from byproducts and starting materials. The method further comprises condensing the alkyl propionate with formaldehyde to produce an alkyl methacrylate.

9 Claims, No Drawings

PROCESSES FOR PRODUCING ETHYLENE AND CARBON MONOXIDE MIXTURES FROM ETHANE

This application claims the benefit of priority under 35 U.S.C. §119(e) of U.S. Provisional Patent Application No. 60/964,733 filed on Aug. 14, 2007.

The present invention relates to a process for producing ethylene and carbon monoxide mixtures from ethane and carbon dioxide, and further to various integrated processes for producing alkyl propionates or methacrylic acid esters from ethane and carbon dioxide.

Ethylene and carbon monoxide mixtures are used as a feedstock for homologation of ethylene to propionic acid derivatives. For example, carbonylation of ethylene to produce methyl propionate, followed by condensation with formaldehyde, is an important commercial route to methyl methacrylate. For example, U.S. Pat. No. 6,284,919 discloses a process for carbonylation of ethylene to methyl propionate. In the first step of this process, ethylene, CO, and methanol feed is converted to methyl propionate. The ethylene and CO feeds used would generally be from conventional sources such as steam cracking and methane steam reforming. However, due to the high cost associated with these ethylene-producing processes, ethylene is a relatively expensive starting material. A process that uses ethane, which is a component of natural gas, as a starting material would be economically desirable due to the large price difference between ethane and ethylene. An integrated process which provides for the production of esters such as methyl propionate and methyl methacrylate using cheap and abundantly available feeds would be of high value.

The problem addressed by this invention is to provide an alternative process for producing mixtures of ethylene and carbon monoxide suitable as a feedstock for other processes.

STATEMENT OF THE INVENTION

The present invention provides a method for producing a mixture of ethylene and carbon monoxide by contacting ethane and carbon dioxide at a temperature of at least 500° C. to produce ethylene and carbon monoxide.

The present invention further comprises steps of: (a) contacting an alcohol, and the ethylene and carbon monoxide with an ethylene carbonylation catalyst to produce an alkyl propionate; and (b) separating the alkyl propionate from byproducts and starting materials, thus providing an integrated process for producing an alkyl propionate. The invention further comprises condensing the alkyl propionate with formaldehyde, thus providing an integrated process for producing methacrylic acid esters. The invention further comprises converting the ethylene and carbon monoxide to copolymers. The invention further comprises combining the ethylene and carbon monoxide with hydrogen to produce propionaldehyde, and optionally, condensing propionaldehyde with formaldehyde to produce methacrolein.

DETAILED DESCRIPTION OF THE INVENTION

Percentages are weight percentages, and temperatures are in ° C., unless specified otherwise. An alkyl group is a saturated hydrocarbyl group having from one to twenty carbon atoms, and may be linear or branched. Preferably, alkyl groups have from one to eight carbon atoms, alternatively from one to four carbon atoms, alternatively one or two carbon atoms, alternatively one carbon atom. The alcohol used in the ethylene carbonylation reaction corresponds to an alkyl group, as defined above, substituted with a hydroxyl group.

In some embodiments of the invention, the catalyst used in the reaction of ethane and carbon dioxide is selected from: (a) a catalyst comprising one or more metals selected from Pt, Pd, Rh, Ir and Ru; and (b) a catalyst comprising at least one oxide of a metal selected from Li, Mo, W, V, Nb, Sb, Sn, Ga, Zr, Mg, Mn, Ni, Co, Ce and rare earth metals.

In some embodiments of this invention, a mixed-metal oxide ("MMO") catalyst is used as the catalyst in the reaction of ethane and carbon dioxide. The general empirical formula for the MMO catalysts is $A_a D_b E_c X_d O_e$, wherein A is at least one element selected from the group consisting of Mo and W, D is at least one element selected from the group consisting of V and Ce, E is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Ag, Pb, P, Pm, Eu, Gd, Dy, Ho, Er, Tm, Yb and Lu; and a=1, b=0.01 to 1.0, c=0.01 to 1.0, d=0.01 to 1.0, and e is dependent on the oxidation state of elements other than oxygen.

Preferably, when a=1, b=0.1 to 0.5, c=0.05 to 0.5 and d=0.01 to 0.5. More preferably, when a=1, b=0.15 to 0.45, c=0.05 to 0.45 and d=0.05 to 0.2. The value of e, i.e. the amount of oxygen present, is dependent on the oxidation state of the other elements in the catalyst. However, e is typically in the range of from 3 to 4.7. Preferably, A is Mo. Preferably, D is V. Preferably, E is Te. Preferably, X is Nb or Ta; and most preferably, X is Nb. In one preferred embodiment of the invention, the catalyst is $Mo_a V_b Te_c Nb_d O_e$.

MMO catalysts and their preparation have been reported, for example, in U.S. Pat. Nos. 6,982,343 and 7,049,466.

Preferably, the ethane and carbon dioxide are contacted at a temperature from 500° C. to 1000° C. In embodiments where a catalyst is used, preferably the temperature is from 550° C. to 800° C., alternatively from 600° C. to 700° C. Preferably, the flow rate is from 100 to 5000 $hr^{-1}$ total gas hourly space velocity (GHSV), alternatively from 500 to 2500 $hr^{-1}$ GHSV, alternatively from 1000 to 2000 $hr^{-1}$ GHSV.

In embodiments where no catalyst is used in the ethane-carbon dioxide reaction, preferably the ethane and carbon dioxide are contacted at a temperature from 600° C. to 750° C. Preferably, the flow rate is from 0.1 to 10 L/min, alternatively from 1 to 3 L/min.

In addition to ethane and carbon dioxide, inert carrier gasses may be present, e.g., nitrogen. Inert carriers do not participate in, and are unaffected by, the reactions of concern.

Catalysts may include support materials, e.g. alumina, silica, silicon carbide, magnesia, zirconia, titania, and combinations thereof, as well as a carrier, such as a monolithic carrier comprising, e.g., cordierite, metal or ceramic. Supports may be modified, stabilized or pretreated to achieve structural stability under the operating conditions.

Ethylene carbonylation catalysts and conditions are well known, and are described, e.g., in U.S. Pat. No. 6,284,919. Typical catalysts include, e.g., those having a Group VIII metal, e.g. palladium, and a phosphine ligand, e.g. an alkyl phosphine, cycloalkyl phosphine, aryl phosphine, pyridyl phosphine or bidentate phosphine.

In some embodiments of the invention, the products of reaction of ethane and carbon dioxide, which comprise ethylene and carbon monoxide, are contacted with an ethylene carbonylation catalyst, along with an alcohol. The ethylene and carbon monoxide stream may be passed into a different reactor for carbonylation, or alternatively, into another portion of the same reactor. The alkyl propionate product can be converted to an alkyl acrylate in an oxidative dehydrogenation process.

Unreacted ethane and carbon dioxide may be present in the product stream from reaction of ethane and carbon dioxide, as well as in the product stream from carbonylation. After separation of the carbonylation product stream, ethane and carbon oxides may be recycled to the input of the reaction of ethane and carbon dioxide. Trace amounts of ethylene and alcohol may also be present. Unreacted ethylene and alcohol from the carbonylation reaction may be recycled to the input of the carbonylation reaction.

In some embodiments of the invention, the alcohol is methanol, the alkyl propionate is methyl propionate and the alkyl methacrylate is methyl methacrylate. In these embodiments, the method represents an integrated process for producing methyl methacrylate starting from ethane and carbon dioxide.

In some embodiments of the invention, the ethylene and carbon monoxide products from the reaction of ethane and carbon dioxide are subjected to a hydroformylation reaction to produce propionaldehyde, as described, e.g., in U.S. Pat. No. 4,408,079. The propionaldehyde product can be oxidized to propionic acid or condensed with formaldehyde to produce methacrolein, which in turn can be used to produce methacrylic acid.

In some embodiments of the invention, the method further comprises polymerization of the methyl methacrylate product to provide an integrated process for producing methyl methacrylate polymers or copolymers starting from ethane and carbon dioxide.

In some embodiments of the invention, methanol is used to produce methyl methacrylate as described herein, and the methyl methacrylate then is transesterified with other alcohols to produce other alkyl methacrylates.

In some embodiments of the invention, the ethylene and carbon monoxide are copolymerized. Preferably, a palladium compound is used as a catalyst, e.g., palladium cyanide, aryl phosphine complexes of palladium or palladium halides, or tetrakis triarylphosphine platinum complex. Polymerization processes are described, e.g., in U.S. Pat. Nos. 3,530,109 and 3,694,412. The ethylene-carbon monoxide polymer can be converted to a thermosetting compound by heating.

In some embodiments of the invention, ethane, carbon dioxide and oxygen are reacted under millisecond contact times resulting in an autothermal reaction. Millisecond contact times are times less than one second, alternatively less than 900 milliseconds, alternatively less than 500 milliseconds, alternatively less than 100 milliseconds, alternatively less than 50 milliseconds, alternatively less than 10 milliseconds. In some embodiments of the invention, ethane and carbon dioxide react either in a single reactor or in staged reactors to provide improved heat balance.

EXAMPLES

Example 1

Ethane Conversion with Catalyst

The catalyst used was a Mo/V/Te/Nb mixed metal oxide prepared as previously reported in U.S. Pat. No. 6,982,343.
Catalytic experiments were carried out using 4 mL of catalyst diluted with 4 mL of silicon carbide chips charged to a ½" (12.7 mm) O.D. stainless steel reactor tube. The reactor was heated to 675° C. in flowing $N_2$. Once at 675° C., a feed comprising $C_2H_6$:$CO_2$:$N_2$ in a 1:3:1 molar ratio was introduced into the reactor. The gases were fed at 100 mL/min total (ethane: 20 mL/min, $CO_2$: 60 mL/min, and $N_2$: 20 mL/min). Analysis of the products was by GC and $N_2$ was employed as an internal standard. Feed conversions and product yields were calculated on a molar basis. Data obtained from the experiment described above are given below.

| Time on stream, hrs | $C_2H_6$ conversion, % | $C_2H_4$ yield, % | CO yield, % |
|---|---|---|---|
| 0.5 | 38.0 | 13.5 | 4.3 |
| 1.0 | 20.5 | 15.5 | 5.2 |
| 1.5 | 19.8 | 15.2 | 4.9 |
| 2.0 | 18.4 | 14.5 | 4.5 |
| 2.5 | 16.5 | 13.6 | 4.0 |
| 3.0 | 14.5 | 12.3 | 3.4 |
| 3.5 | 9.5 | 10.9 | 2.8 |
| 4.0 | 7.3 | 9.3 | 2.2 |
| 4.5 | 5.7 | 7.5 | 1.7 |

The data clearly show that desired ethylene and CO products from the process are formed in quantities suitable for further processing to methyl propionate.

The invention claimed is:

1. A method for producing a mixture of ethylene and carbon monoxide by contacting ethane and carbon dioxide at a temperature of at least 500° C. to produce ethylene and carbon monoxide; wherein the ethane and carbon dioxide are contacted with a MMO catalyst having empirical formula $A_aD_bE_cX_dO_e$, wherein A is at least one element selected from the group consisting of Mo and W, D is at least one element selected from the group consisting of V and Ce, E is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Ag, Pb, P, Pm, Eu, Gd, Dy, Ho, Er, Tm, Yb and Lu; and a=1, b=0.01 to 1.0, c=0.01 to 1.0, d=0.01 to 1.0, and e is dependent on the oxidation state of elements other than oxygen.

2. The method of claim 1 in which the MMO catalyst is $Mo_aV_bTe_cNb_dO_e$ and the temperature is from 600° C. to 700° C.

3. The method of claim 1, further comprising steps of:
 (a) contacting an alcohol, and said ethylene and carbon monoxide with an ethylene carbonylation catalyst to produce an alkyl propionate; and
 (b) separating the alkyl propionate from byproducts and starting materials.

4. The method of claim 3, further comprising reacting the alkyl propionate with formaldehyde to produce an alkyl methacrylate.

5. The method of claim 4 in which the alcohol is methanol, the alkyl propionate is methyl propionate and the alkyl methacrylate is methyl methacrylate.

6. The method of claim 5, further comprising polymerizing the methyl methacrylate.

7. The method of claim 1, further comprising co-polymerizing the ethylene and carbon monoxide.

8. The method of claim 1, further comprising combining said ethylene and carbon monoxide with hydrogen to produce propionaldehyde.

9. The method of claim 8, further comprising condensing the propionaldehyde with formaldehyde to produce methacrolein.

* * * * *